United States Patent [19]

Watkins et al.

[11] Patent Number: 5,156,163

[45] Date of Patent: Oct. 20, 1992

[54] PATELLA DISPLACEMENT MEASURING DEVICE

[75] Inventors: K. Richard Watkins, San Diego; Dale M. Daniels, La Mesa, both of Calif.

[73] Assignee: MEDmetric Corporation, San Diego, Calif.

[21] Appl. No.: 692,165

[22] Filed: Apr. 26, 1991

[51] Int. Cl.⁵ ............................................. A61B 5/103
[52] U.S. Cl. ................................................. 128/782
[58] Field of Search ............. 128/774, 782; 33/512, 33/511; 73/379, 380, 381

[56] References Cited

U.S. PATENT DOCUMENTS

| | | | |
|---|---|---|---|
| 3,680,386 | 8/1972 | Cannon | 73/379 R |
| 4,296,744 | 10/1981 | Palumbo | 128/80 C |
| 4,501,266 | 2/1985 | McDaniel | 128/69 |
| 4,534,364 | 8/1985 | Lamoreux | 128/774 |
| 4,583,554 | 4/1986 | Mittelman et al. | 128/774 |
| 4,583,555 | 4/1986 | Malcom et al. | 128/782 |
| 4,649,934 | 3/1987 | Fraser et al. | 128/782 |
| 4,799,497 | 1/1989 | Riley | 128/774 |
| 4,969,471 | 11/1990 | Daniel et al. | 128/774 |

Primary Examiner—Max Hindenburg
Assistant Examiner—Guy V. Tucker
Attorney, Agent, or Firm—Nydegger & Associates

[57] ABSTRACT

A device for evaluating the integrity of the patella femoral joint measures movement of the patella in response to a lateral force applied against the patella of a flexed leg supported in a relaxed position. The device includes a measuring instrumentality which is positionable against the patella to measure the linear displacement of the patella in response to the lateral force. The magnitude of the applied force is correlated with the degree of leg flexion and the linear displacement of the patella to indicate the health and condition of tissues in the knee which resist dislocation of the patellofemoral joint and which promote alignment of the patella within the joint.

11 Claims, 6 Drawing Sheets

PATELLA DISPLACEMENT MEASURING DEVICE

TECHNICAL FIELD

The present invention relates generally to a medical diagnostic device. More particularly, the present invention relates to a device for diagnosis of patellofemoral instability. The present invention particularly, though not exclusively, relates to a device for measuring linear displacement of the patella when a lateral force is applied thereto.

BACKGROUND OF THE INVENTION

Chondromalacia, osteoarthritis, malalignment, subluxation, patellar instability, and anterior knee pain are all terms relating to specific knee disorders which can be generally characterized as instability of the patellofemoral joint. Among the tools employed to diagnose patellofemoral joint dysfunction, is radiological assessment. However, as pointed out in Teigte, R. A., "Radiology of the Patellofemoral Joint", CPEC, 1985, radiographic evaluation in many cases is unsatisfactory because x-rays of critical views of the joint are omitted or improperly taken. Nonorthopedic personnel often do not have the expertise to perform such x-rays, in which case emergency diagnosis of patellofemoral joint instability may be inadequate. The result can be prolonged recovery or, in the worst case, incomplete recovery.

Given the inherent complexities and risks of radiological assessment, additional diagnostic tools are needed to augment or supplant radiological means in the diagnosis of patellofemoral joint instabilities. Although devices exist for physically evaluating the integrity of the knee, such devices have not proven sufficiently specific for diagnosis of patellofemoral joint instability. As such, physical means are needed for directly acquiring meaningful and reliable diagnostic data specific to the patellofemoral joint. Further, physical means are needed for acquiring diagnostic data specific to the patellofemoral joint in a relatively economical and practical manner. Further, physical means are needed for acquiring diagnostic data specific to the patellofemoral joint which enable accurate and thorough treatment of patellofemoral joint instabilities.

SUMMARY OF THE INVENTION

The present invention is a patella displacement measuring device and a related method for diagnosing the health and condition of tissues in the knee which maintain alignment of the patella within the patellofemoral joint and resist dislocation thereof. The device comprises a patella displacer physician to treat patellofemoral instability. which engages the patella and applies a lateral force thereto. The device further comprises a plurality of measuring instrumentalities for acquiring physical data in response to the application of lateral force to the patella.

The measuring instrumentalities include a force measuring instrumentality and a linear displacement measuring instrumentality. The force measuring instrumentality measures the level of force applied to the patella across the patella displacer. The linear displacement measuring instrumentality measures the extent of patellar linear displacement in response to the lateral force. A data assembler may further be provided in communication with the above-recited measuring instrumentalities to receive the output thereof. The data assembler correlates the measured data to provide a diagnostic description of the integrity of the tissues surrounding the patella. This diagnostic description can be used by a physician to treat patellofemoral instability.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF PREFERRED EMBODIMENTS

Figure 1:
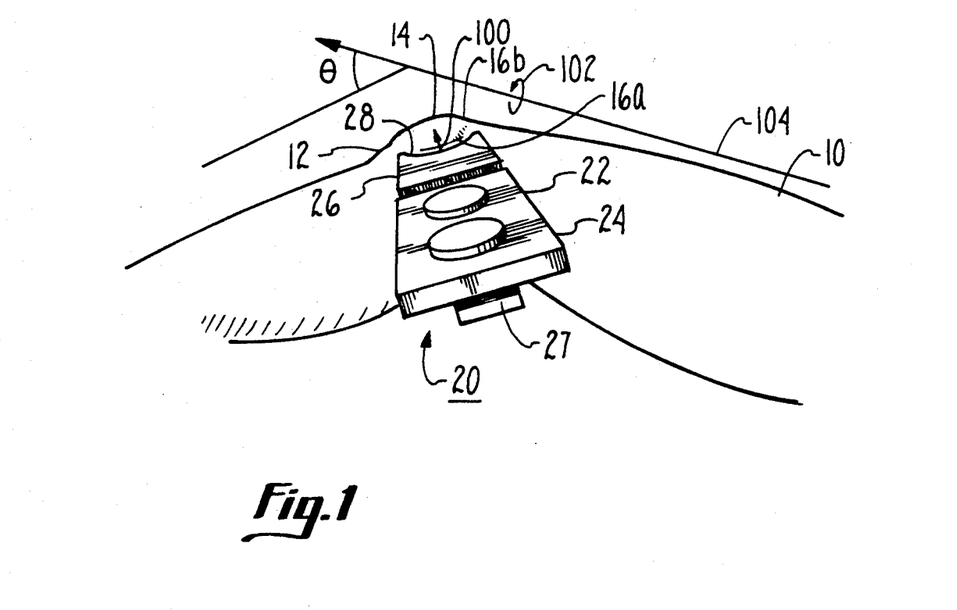
FIG. 1 is a perspective view of the patella displacement measuring device of the present invention, showing the device in position at the knee.

Referring to FIG. 1, a first embodiment of the patella displacement measuring device generally designated as 20 is shown in position at the knee 12 on the left leg 10 of a patient. Device 20 has a patella displacer 22 comprising a base member 24 and a patella engagement member 26. Members 24 and 26 are resiliently connected across a force measuring instrumentality described hereafter. Device 20 further has a linear displacement measuring instrumentality 27 also described hereafter.

Engagement member 26 has a surface 28 which is opposite the points of connection between member 24 and 26. Surface 28 is substantially shaped to conform to surface 16a on the outer side of the patella 14, thereby facilitating engagement of surfaces 16a and 28 when engagement member 26 is positioned laterally adjacent the patella 14. The term "lateral", as used herein in correspondence with the leg 10, knee 12 or patella 14, relates generally to the outer or inner side thereof. Thus, for example, a lateral position with respect to the patella 14 relates either to outer surface 16a or inner surface 16b.

It is apparent from the foregoing that, although patella displacer 22 is shown in FIG. 1 positioned at the outer surface 16a of patella 14, patella displacer 22 is also operable while positioned at the inner surface 16b of patella 14. Either position is within the scope of the term "lateral", as presently defined.

Figure 2:
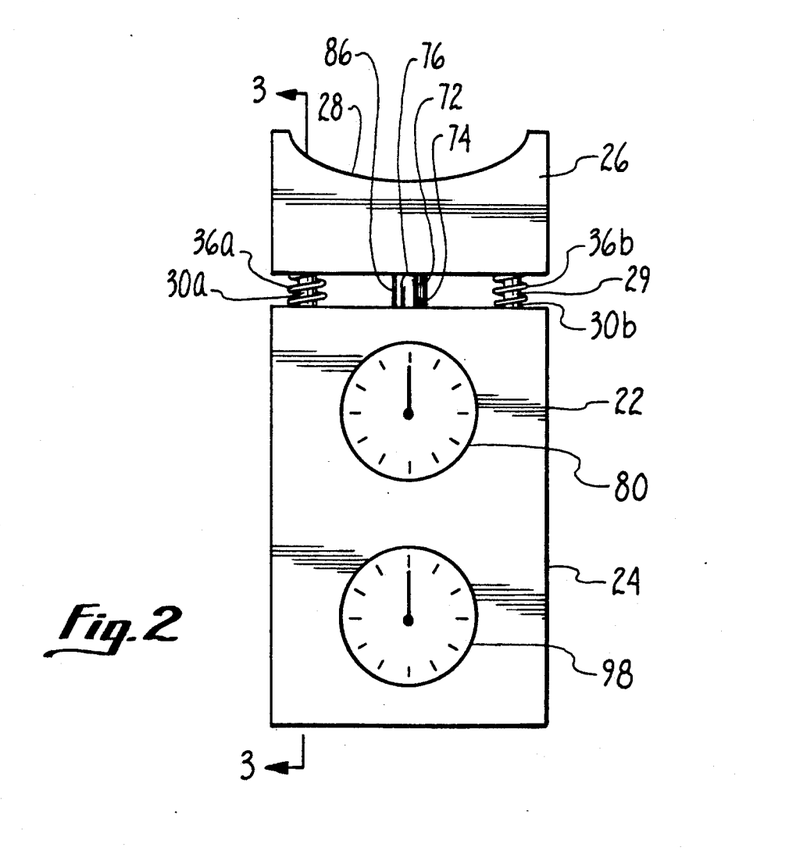
FIG. 2 is a top view of the patella displacement measuring device of the present invention.

FIG. 2 shows patella displacer 22 and the force measuring instrumentality integral therewith. The force measuring instrumentality comprises a resilient connector 29 between base member 24 and engagement member 26. Resilient connector 29 comprises two pairings of slidable cylindrical shafts 30a and 30b and compression springs 36a and 36b, each pairing being positioned on opposite sides of patella displacer 22. One shaft-spring pairing 30a, 36a and related cooperative structure is shown in detail in FIG. 3, which is referred to below.

Figure 3:
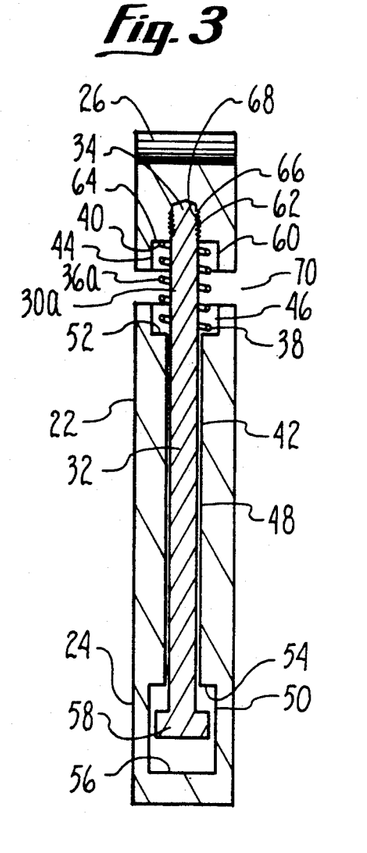
FIG. 3 is a cross-sectional view of the patella displacement measuring device of the present invention as seen along line 3—3 in FIG. 2.

Shaft 30a has two ends 32 and 34 and spring 36a likewise has two ends 38 and 40. Ends 32 and 38 are disposed within a cylindrical bore 42 of base member 24, while ends 34 and 40 are disposed within a cylindrical bore 44 of engagement member 26. Bore 42 has three stages 46, 48, and 50, which are characterized by middle stage 48 having a diameter less than that of either first stage 46 or end stage 50. The intersection of stages 46 and 48 forms shoulder 52. First stage 46 is open to the outside and houses spring end 38. Stage 46 has a diameter slightly greater than spring 36a, while stage 48 has a diameter less than spring end 38, thereby enabling spring 36a to be compressed within stage 46 with shoulder 52 acting as a stop for spring end 38.

Middle stage 48 has a diameter less than the diameter of spring 36a, but slightly greater than that of shaft 30a. End stage 50 has substantially the same diameter as first stage 46 and, as noted above, a diameter greater than stage 48 intersection of stages 48 and 50 forms shoulder 54, while the opposite end 56 of stage 50 is closed. Stage 50 houses flange 58 which is the terminus of shaft end 32. Flange is slightly smaller in diameter than stage 50, but larger in diameter than stage 48. Thus, shoulder 54 is a stop for flange 58, thereby slidably retaining shaft end 32 in bore 42.

Bore 44 has two stages 60 and 62, which are characterized by end stage 62 having a diameter less than that of first stage 60. The intersection of stages 60 and 62 forms shoulder 64. First stage 60 is open to the outside and houses spring end 40. Stage 60a has a diameter slightly greater than spring 36a, while end stage 62 has a diameter less than spring end 40, thereby enabling spring 36a to be compressed within stage 60 with shoulder 64 acting as a stop for spring end 40.

End stage 62 has internal threads 66 which are sized and positioned to receive external threads 68 at the terminus of shaft end 34. Consequently, shaft end 34 is fixably secured within bore 44 by screwing threads 68 into 66.

Shaft 30a, bores 42 and 44, and spring 36a are correspondingly dimensioned such that, upon assembly of patella displacer 22, shaft 30a is axially and slidably disposed through spring 36a while spring ends 38 and 40 are biased against shoulders 52 and 64, respectively. Spring 36a further biases flange 58 against shoulder 64 to provide a gap 70 of a predetermined length between base member 24 and engagement member 26 when device 20 is in an extended inoperative position. Thus, the range across which shaft 30a is freely slidable within bore 42 and spring 36a is between the inoperative extended position defined by abutment of flange 58 against shoulder 64 and an operative compressed position defined by abutment of engagement member 26 against base member 24.

Referring back to FIG. 2, the second shaft-spring pairing 30b, 36b shown opposite first pairing 30a, 36a is provided with internal structure, not shown, but identical to that of first pairing 30a, 36a. As is further apparent, it is within the scope of the present invention to reverse the axial orientation of shafts 30a and 30b and the cooperative internal structure of members 24 and 26 such that shafts 30a and 30b are fixed within member 24 and slidable within member 26.

The force measuring instrumentality shown in FIG. 2 further comprises a force gauge 72 which includes a projectile 74 having two ends. End 76 abuts engagement member 26 across gap 70. The other end not shown is slidably disposed within base member 24 to engage a conventional force display mounted on base member 24. Operative details of force gauge 72, including details of projectile 74 and display so, are not shown, but are within the purview of the skilled artisan, and provide means for translation of linear deviations from the predetermined length of gap 70 into values of lateral force applied against patella 14.

Figure 4:
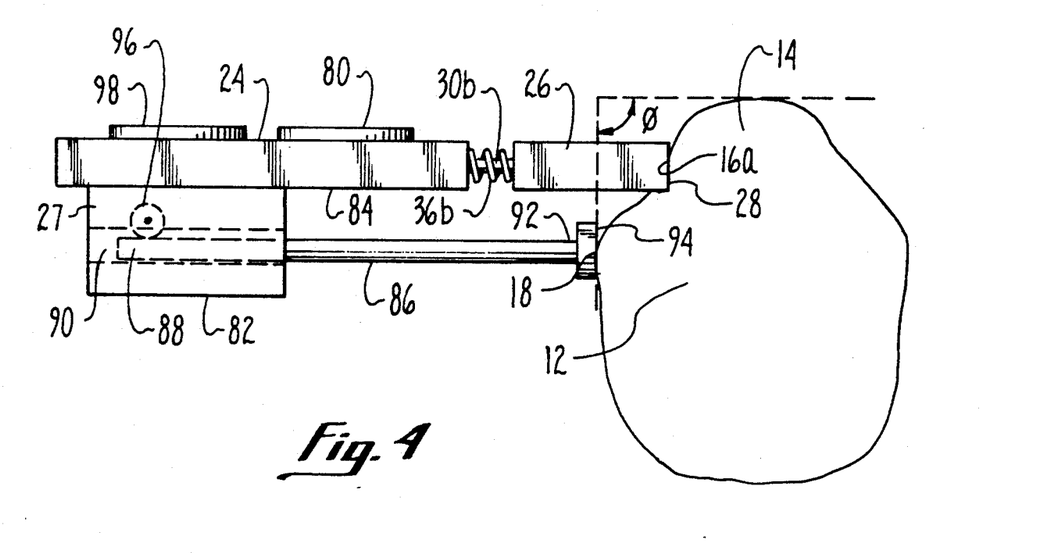
FIG. 4 is a side view of the patella displacement measuring device of the present invention.

FIG. 4 shows patella displacer 22 and linear displacement measuring instrumentality 27 integral therewith. Linear displacement measuring instrumentality 27 comprises a mount 82 connected to the underside 84 of base member 24. A rod 86 has an end 88 slidably disposed within a bore 90 through mount 82. The opposite end 92 has a face 94 which laterally engages the knee 12 below the patella 14. Bore 90 is preferably positioned in mount 82 at a depth below base member 24 such that face 94 engages the knee 12 at the femoral condyle 18 when surface 28 engages patella surface 16a.

Linear displacement measuring instrumentality 27 further comprises a wheel 96 which rotatably engages end 88 as well as a conventional linear displacement display 98 mounted on base member 24. End 88 rotates wheel 96 as it slides through bore 90, thereby providing a resistance to end 88 sliding therethrough. Operative details of wheel 96 and display 98, are not shown, but are within the purview of the skilled artisan, and provide means for translation of displacement of rod 86 into quantitative values of patellar linear displacement.

Referring to FIG. 1 operation of device 20 is provided by placing the leg 10 on a support surface not shown, such as an examination table, with the leg muscles relaxed and the knee 12 posteriorly supported. The knee 12 is preferably maintained at a flexion angle $\Theta$ defined by the intersection of two lines drawn substantially through the femur and tibia of leg 10. The flexion angle $\Theta$ is preferable greater than about 0 degrees The flexion angle $\Theta$ is measured and recorded using a goniometer. Full muscle relaxation can be verified by means of an electromyography sensor applied to the quadriceps.

Referring now to FIGS. 2-4, device 20 is positioned laterally at the knee 12 of the relaxed leg so that conformed surface 28 engages patella surface 16a and face 94 engages the femoral condyle 18. A lateral force is applied to the patella 14 by applying an external force to base member 24 and transmitting the force across resilient connector 29 and engagement member 26 to surface 28. The preferred external force is a manual force applied by the operator of the device 20 while it is hand-held. Thus, base member 24 is preferably sized to be gripped by the hand of the operator.

Springs 36a and 36b compress in response to the lateral force causing projectile 74 and shafts 30a and 30b to retract into base member 24. Gap 70 correspondingly deviates from its predetermined length to a shorter length. In cooperation with displacement of projectile 74, display 80 registers a quantitative value of the magnitude of lateral force applied to the patella 14.

As the lateral force is applied to the patella surface 16a, the patella 14 as well as patella displacer 22 and mount 82 are linearly displaced in the direction of arrow 100 as shown in FIG. 1. However, the femoral condyle 18 remains substantially stationary relative thereto. Rod 86 pushes against the immovable femoral condyle 18 and is displaced through bore 90 in the opposite direction of arrow 100. As a result, wheel 96 rotates and display 98 registers a quantitative value of linear displacement of the patella 14.

The magnitude of the applied lateral force can then be correlated with the values of flexion angle and linear displacement of the patella 14. The correlation data is indicative of the health and condition of tissues in the knee which resist dislocation of the patellofemoral joint and which promote alignment of the patella within the joint.

Although mechanical means are shown herein for measuring linear deviations in gap 70, for translating the deviations into values of lateral force, and for displaying the same, such operations may be performed by electronic means known to those skilled in the art. Likewise, mechanical means for measuring the displacement of rod 86, for translating the displacement of rod 86 into patellar linear displacement, and for displaying the same, may be substituted by conventional electronic means known to those skilled in the art.

Figure 5:
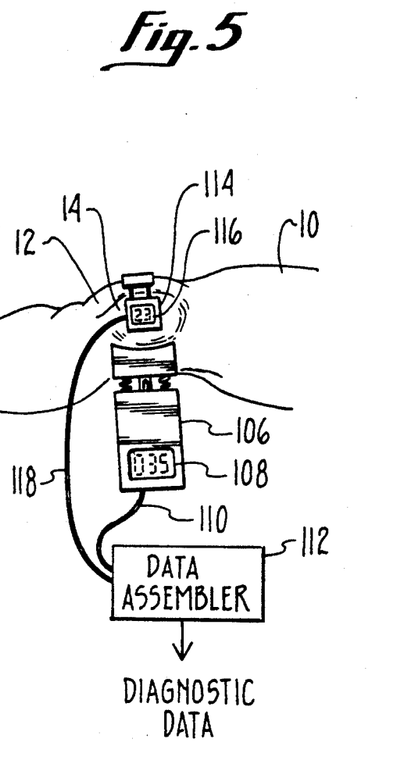
FIG. 5 is a schematic of an embodiment of the patella displacement measuring device of the present invention, wherein electronic means are provided for accumulation and processing of the diagnostic data.

FIG. 5 shows a system schematically, wherein the device designated generally as 106 is substantially similar to that shown in FIGS. 1-4 that conventional electronic means are substituted for mechanical means to record and display the physical measurements. In addition to feeding electronic data display 108, electrical signals generated by such electronic means may be communicated from device 106 across communication line 110 to data assembler 112 which correlates the signals to generate a relevant diagnostic description of the integrity of the tissues surrounding the patella. Data assembler 112 used herein may be selected from conventional microprocessors known to one skilled in the art. Data assembler 112 may be integral with device 106 or remote therefrom.

FIG. 5 further shows a goniometer 114 which may be provided in conjunction with device 20 of FIG. 1 or device 106 of FIG. 5. Because the tissue of the knee 12 limits the linear displacement of the patella 14, the lateral force applied to the patella surface 16a may also cause an angular displacement of the patella 14. The angular displacement is the degree of rotation of the patella 14 in the direction of arrow 102 about an axis 104 substantially parallel to the proximal-distal axis of the femur as shown in FIG. 1. Goniometer 114 quantitatively measures this displacement as a deviation in angle $\phi$, shown in FIG. 4, from 90° as the patella 14 is rotated.

Accordingly, goniometer 114 is shown engaging the patella 14 and a point on the knee 12 which is fixed relative to the patella 14. Goniometer 114 has a display 116 for recording quantitative values of angular displacement $\phi$ of the patella 14 relative to the remainder of the knee 12. Goniometer 114 may further be in communication with data assembler 112 via line 118 so that the values of angular displacement $\phi$ may additionally be correlated with values of the leg flexion $\Theta$ and linear displacement in characterizing the condition of the knee.

Figure 6:
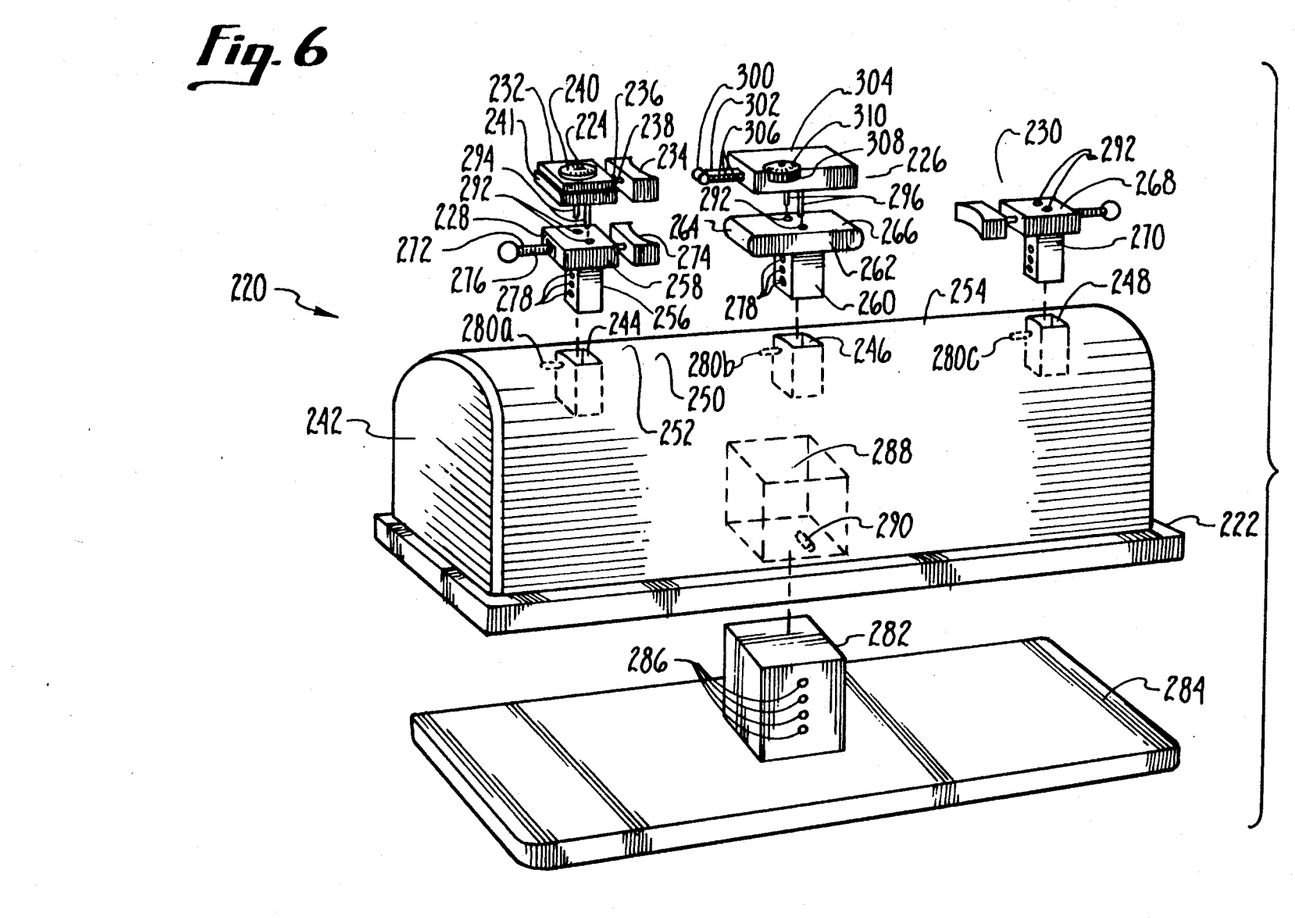
FIG. 6 is an exploded perspective of an embodiment of the patella displacement measuring device of the present invention, wherein the linear displacement measuring instrumentality is opposite the patella displacer.

A second embodiment of the patella displacement measuring device of the present invention is described with reference to FIG. 6 showing the patella displacement measuring device designated generally as 220, device 220 comprises posterior knee support 222 having mounted thereon a patella displacer 224, a linear displacement measuring instrumentality 226, and a pair of femoral clamps 228 and 230. Patella displacer 224 is substantially similar to patella displacer 22 of the first embodiment shown in FIGS. 1-4. Patella displacer 224 comprises base member 232, engagement member 234, spring 236-shaft 238 pairing, and force gauge 240 which are structurally and operationally identical to the analogous components of device 20. Displacer 224 is slidably housed in a guide frame 241.

Posterior knee support 222 comprises a bolster 242 having three slots 244, 246, 248 in its top surface 250. Top surface 250 has a portion 252 lying between slots 244 and 246 which posteriorly abuts one knee 12a of the patient and further has a portion 254 lying between slots 246 and 248 which posteriorly abuts the other knee 12b of the patient. Accordingly, slot 244 is positioned to receive a post 256 extending from adjustable femoral condyle restraint 258 of femoral clamp 228. Slot 246 is positioned to receive a post 260 extending from stationary femoral condyle restraint 262. Restraint 262 has one surface 264 to cooperate with adjustable restraint 258, thereby forming femoral clamp 228, and has another surface 266 to cooperate with a second adjustable femoral condyle restraint 268, thereby forming femoral clamp 230. Second adjustable restraint 268 has a post 270 receivable with slot 248. Thus, femoral clamps 228, 230 are positioned side by side to simultaneously secure both knees 12a, 12b of a patient.

Adjustable restraint 258 is provided with a slidable control arm 272 connected to an adjustable surface 274 across a ratchet 276 releasably biasing against outward displacement of control arm 272. Second adjustable restraint 268 is identically provided. Posts 256, 260, 270 each have a plurality of vertically-spaced holes 272 formed therein to receive releasable spring loaded pins 280 a,b,c mounted in each of slots 244, 246, 248 respectively for height adjustment of clamps 228, 230. Bolster 242 is likewise provided with a post 282 mounted on a base 284, holes 286 formed in post 282, a slot 288 formed in bolster 242 to receive post 282, and a spring loaded pin 290 disposed in slot 288 to enable height adjustment of the entire knee support assembly 222. A pair of spaced openings 292 are provided in each of adjustable restraints 258, 262, 268 to receive pins 294 extending from a guide frame 295 which slidably houses patella displacer 224 or to receive pins 296 extending from instrumentality 226. Pins 294, 296 enable removable mounting of displacer 224 or instrumentality 226 on either restraint 258, 262, or 268.

Linear displacement measuring instrumentality 226 comprises a contact pad 300 affixed to a toothed shaft 302 slidably extending from a housing 304. Teeth 306 of shaft 302 align with a toothed gear 308 rotatably mounted in housing 304 such that when shaft 302 slides into or out of housing 304, teeth 306 correspondingly turn gear 308. A drive shaft not shown connects gear 308 to a calibrated linear displacement display wheel 310 rotatably mounted on housing 304.

Figure 7:
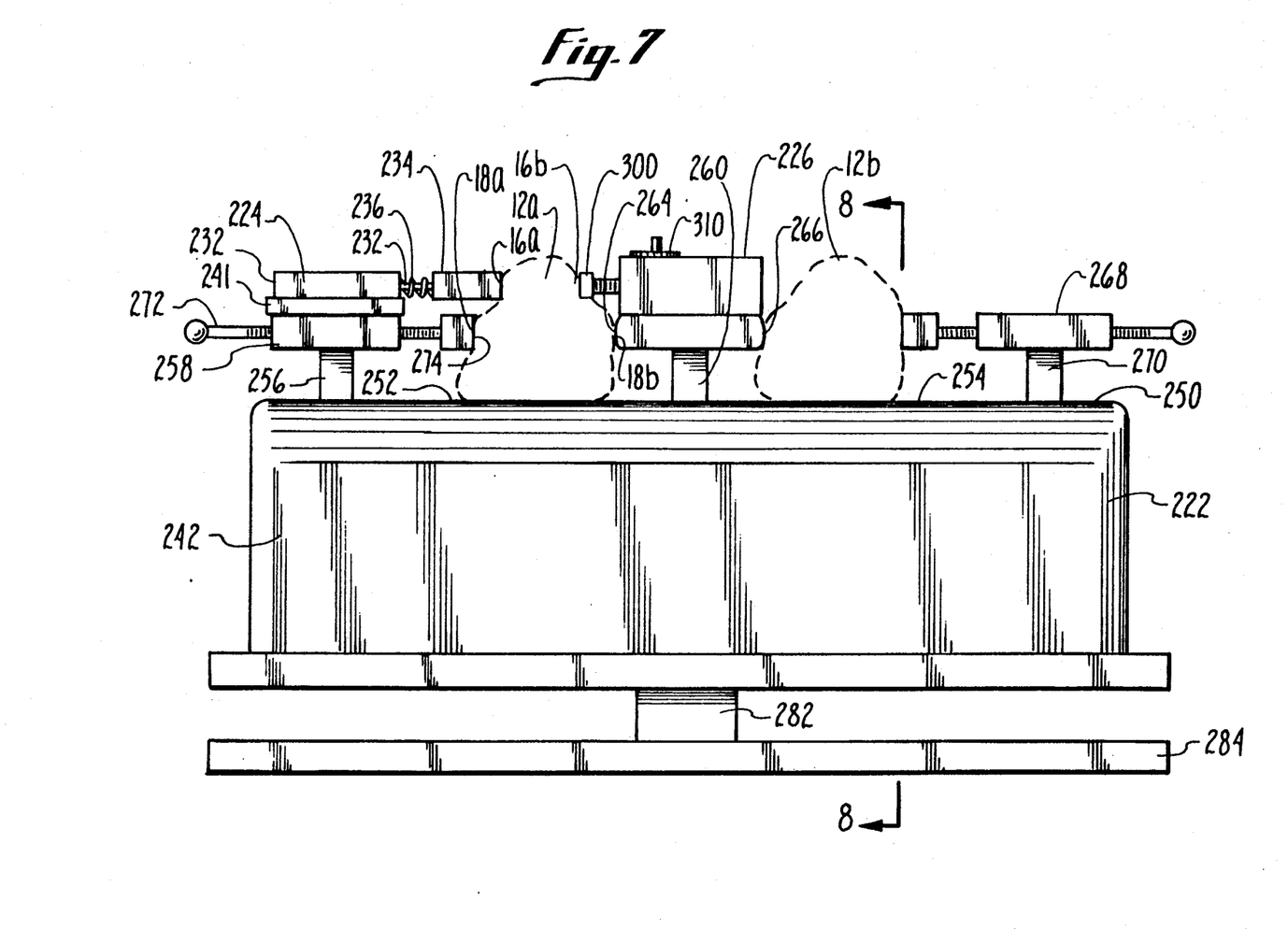
FIG. 7 is a front view of an embodiment of the patella displacement measuring device of the present invention, wherein the linear displacement measuring instrumentality is opposite the patella displacer.
Figure 8:
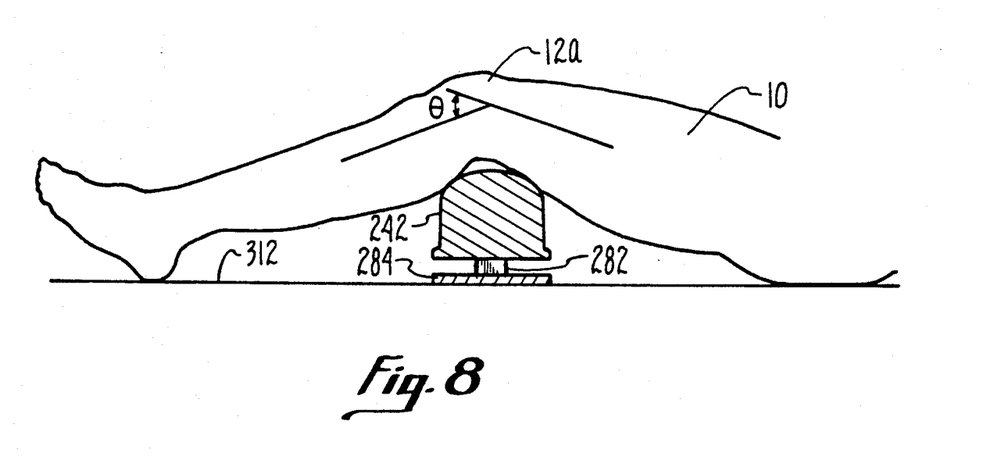
FIG. 8 is a cross-sectional side view of the patella displacement measuring device of the present invention as seen along line 8—8 in FIG. 7.

Operation of the device 220 is described with reference to FIGS. 7 and 8. In operation, the left and right knees 12a, 12b are shown in FIG. 7 to be posteriorly positioned on portions 252, 254 respectively of surface 250. The height of bolster 242 is set by adjustment of post 282 so that the knee 12a assumes a desired angle of flexion Θ as shown in FIG. 8. A flexion angle Θ within the preferred range set forth herein enables acquisition of meaningful patellar stability data while the patient reclines on an examination surface 308 with the quadriceps muscles in a substantially relaxed condition.

Referring back to FIG. 7, once the knees 12a, 12b are properly positioned on bolster 242, they are secured by femoral clamps 228, 230. Clamp 228 is tightened onto knee 12a by adjusting the height of posts 256, 260 such that restraint surfaces 264, 274 align with the femoral condyles 18a 18b of the knee 12a and displacer 224 and instrumentality 226 correspondingly align with the lateral surfaces 16a, 16b of the patella 14. Femoral condyle 18b is then abutted against stationary surface 264 while arm 272 is ratcheted inwardly to bring adjustable surface 274 into tight engagement with femoral condyle 18a, thereby minimizing rotation of knee 12a when a linear force is applied to the lateral surface 16 of the patella 14. Knee 12b is secured by clamp 230 in substantially the same manner.

Diagnosis of knee 12a is performed by mounting guide frame 241 on restraint 258 and mounting instrumentality 226 on restraint 226 in opposition to displacer 224. Contact pad 300 is placed against surface 16b and calibrated wheel 310 is zeroed. A lateral force is applied to the patella surface 16a across displacer 224 by manually sliding displacer 224 toward surface 16a in guide frame 241. The magnitude of the force is measured in the same manner as described above with respect to device 20. Linear displacement is measured on calibrated wheel 310 which turns in cooperation with displacement of contact pad 300 away from displacer 224.

The mounting positions of guide frames 241 and instrumentality 226 may then be reversed so that guide frame 241 is mounted on restraint 258 and displacer 224 is mounted on restraint 262 to measure linear patellar displacement of knee 12a in the opposite direction. Diagnosis of knee 12b is performed in substantially the same manner as above by mounting displacer 224 on restraints 262 and 268 and opposingly mounting instrumentality 226 on restraints 268, 262 respectively.

As in the first embodiment of the present invention, the second embodiment permits values of flexion angle, applied force and linear displacement to be alternatively processed and displayed by electronic means, which are provided in communication with the measuring means, in the manner of FIG. 5. Likewise, angular displacement can be measured with a goniometer in cooperation with device 220 in the manner of FIG. 5.

Figure 9:
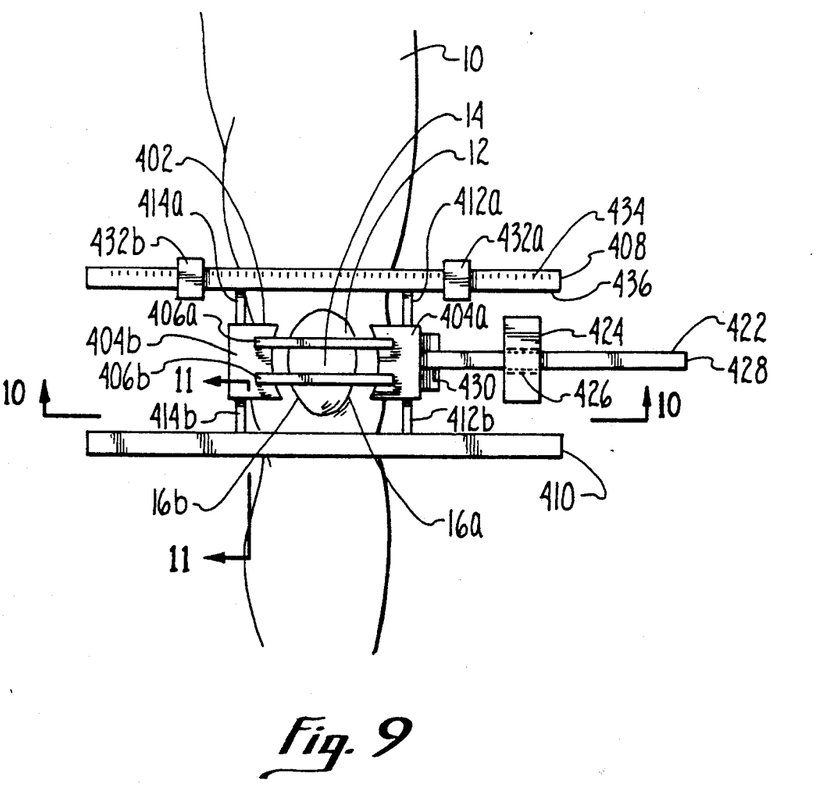
FIG. 9 is a top view of an embodiment of the patella displacement measuring device of the present invention, wherein the patella displacer is reciprocating.
Figure 10:
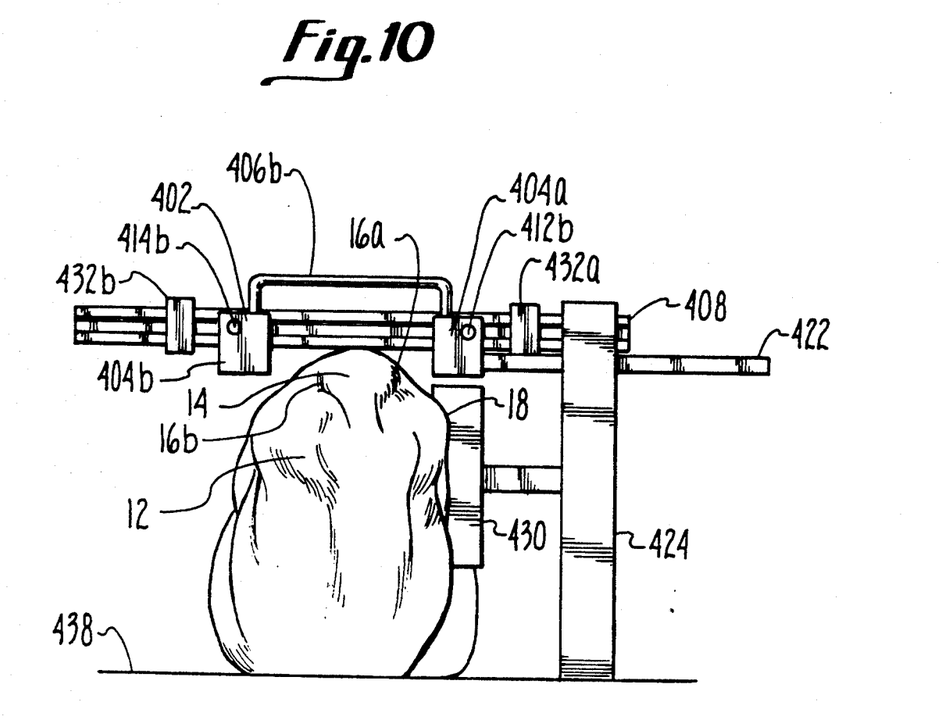
FIG. 10 is a cross-sectional view of the patella displacement measuring device of the present invention as seen along line 10—10 in FIG. 9.
Figure 11:
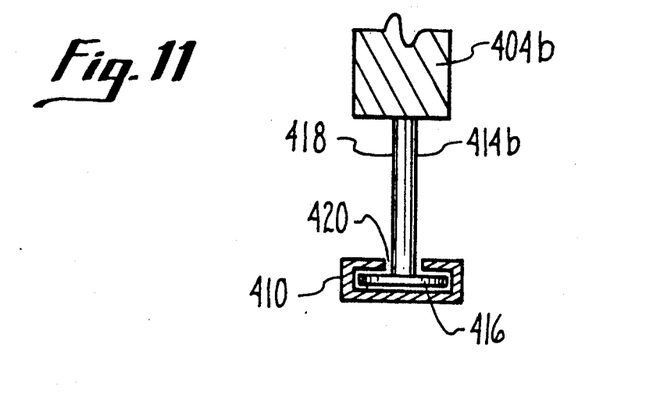
FIG. 11 is a cross-sectional view of the rail and sliding member engagement of the present invention as seen along line 11—11 in FIG. 7.

A third embodiment of the present invention is shown in FIGS. 9-11 and described hereafter. Referring to FIG. 9, the patella displacement measuring device of the third embodiment is designated generally as 100. A patella displacer 402 comprises a pair of engagement members 404a, 404b laterally positioned to straddle patella 14 and engage patella surfaces 16a, 16b, respectively. Members 404a, 404b are connected by rigid crossbars 406a, 406b to maintain members 404a, 404b in fixed relationship to each other as displacer 402 moves relative to the leg 10.

Members 404a, 404b are slidably mounted on parallel rails 408, 410 and positioned therebetween. Mounting of engagement member 404a on rails 408, 410 is provided by sliding members 412a, 412b, respectively, which are affixed to opposite ends of engagement member 404a. Mounting of engagement member 404b on rails 408, 410 is provided in a like manner by sliding members 414a, 414b. FIG. 11 is a cross-section showing the slidable engagement of sliding member 414b to rail 410. Sliding member 414b has an enlarged head 416 which fits within cross-sectionally c-shaped rail 410. Body 418 of member 414b connects to head 416 Within rail 410 through slot 420. Thus, member 414b is free to slide laterally along the path of rail 410. Sliding members 414a, 414c, 414d slidably engage rail 408 or rail 410 in a like manner, thereby enabling linear displacement of engagement members 404a, 404b between rails 408, 410.

Returning to FIG. 7, displacer 402 is further provided With a handle 422 which is connected to engagement member 404a. Handle 422 extends from member 404a through support member 424 via bore 426 such that handle 422 has a free end 428 readily accessible to the operator.

Support member 424 is a stationary support for handle 422 slidable therethrough and for knee stabilizer 430 which fixedly engages the knee 12 below the patella 14, preferably at the femoral condyle 18. A linear displacement measuring instrumentality is further provided integral with rail 408. Such instrumentality includes oval-shaped tabs 432a, 432b, which engage sliding members 412a, 414a to slide over rail 408, and distance calibrations 434 on the top surface 436 of rail 408.

FIG. 8 more clearly shows the relation of the knee 12 to support member 424 as well as handle 422 and stabilizer 430 supported thereby.

In operation, device 400 is placed over the knee 12 such that support member 424 rests on the surface 438 which supports the leg 10 during examination, such as an examination table. Device 400 can be operated in a reciprocating manner by either pulling on handle 422 to engage member 404b with patella surface 16b or pushing on handle 422 to engage member 404a with surface 16a.

In the pulling mode, tab 432a is positioned against sliding member 412a and calibrations 434 are referenced while stabilizer 430 is laterally positioned against the femoral condyle 18. A lateral pulling force is applied to handle 422. Linear displacement of the patella 14 is recorded by deviation of tab 432a from the reference calibration. Conversely, in the pushing mode, tab 432b is positioned against sliding member 414a and calibrations 434 are referenced. When a lateral pushing force is applied to handle 422, linear displacement of the patella 14 is recorded by deviation of tab 432b from the reference calibration.

Although device 400 has only been described with respect to the linear displacement measuring instrumentality, it is evident to one skilled in the art that the force and angular displacement measuring means and data assembler of the first embodiment can readily be adapted to device 400 and fall within the scope thereof.

While a particular PATELLA DISPLACEMENT MEASURING DEVICE as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. A patella displacement measuring device comprising:
   a bolster;
   a first clamp member and a second clamp member opposingly mounted on said bolster, said first and second clamp members having a space formed therebetween to receive the leg of a subject;
   a patella displacer connectively mounted to said bolster, thereby positioned adjacent the patella, said patella displacer including a patella engagement member having a surface to laterally engage the patella and apply a lateral force thereto, a base member linearly displaceable relative to said bolster and engageable with an external source of said lateral force, and means for resiliently connecting said base member to said engagement member; and
   a linear displacement measuring instrumentality connectively mounted to said bolster, thereby positioned adjacent the patella and opposite said patella displacer, for measuring the linear displacement of the patella resulting from said lateral force said instrumentality including a displacement member and having a surface to laterally engage the patella, said instrumentality further including a housing to support said movable displacement member, said housing being linearly displaceable relative to said bolster.

2. The patella displacement measuring device as recited in claim 1 wherein said resilient connecting means comprises a compression spring fixably engaging said base member and said engagement member at opposite ends of said spring.

3. The patella displacement measuring device as recited in claim 1 wherein said resilient connecting means comprises a shaft slidably engaging said base member and said engagement member at opposite ends of said shaft.

4. The patella displacement measuring device as recited in claim 1 wherein said instrumentality further includes a means for displaying values of said linear displacement of said displacement member.

5. The patella displacement measuring device as recited in claim 1 wherein said bolster is positionable behind the knee to support the knee at a predetermined angle of flexion.

6. The patella displacement measuring device as recited in claim 1 wherein said displacement member is a rod slidably housed by said housing.

7. A patella displacement measuring device as recited in claim 1 further comprising a third clamp member and a fourth clamp member opposingly mounted on said bolster, said third and fourth clamp members having an additional space formed therebetween the receive the other leg of the subject.

8. A patella displacement measuring device as recited in claim 7 wherein said patella displacer is connectively mounted to said bolster across said first clamp member and said measuring instrumentality is mounted to said bolster across said second clamp member.

9. A patella displacement measuring device as recited in claim 8 wherein said patella displacer is interchangeably mountable on said first or fourth clamp member and said measuring instrumentality is interchangeably mountable on said second or third clamp member.

10. A patella displacement measuring device as recited in claim 1 wherein said patella displacer is connectively mounted to said bolster across said first clamp member and said measuring instrumentality is mounted to said bolster across said second clamp member.

11. A patella displacement measuring device comprising:
    a patella engagement member having a surface to laterally engage the patella and apply a lateral force thereto;
    a bolster positionable behind the knee;
    a first clamp member and a second clamp member opposingly mounted on said bolster, said first and second clamp members having a space formed therebetween to receive the leg of a subject;
    a base member slidably mounted to said bolster and engageable with a source of said lateral force;
    a compression spring resiliently connecting said base member to said engagement member;
    a force gauge for measuring the lateral force applied to the patella; and
    a linear displacement measuring means slidably mounted to said bolster and laterally engaging the patella on the opposite side of the leg as said engagement member surface laterally engages the patella.

* * * * *